(12) United States Patent
King

(10) Patent No.: US 10,987,446 B2
(45) Date of Patent: Apr. 27, 2021

(54) PORTABLE AIR FRESHENER DEVICE

(71) Applicant: William James King, Orange, CA (US)

(72) Inventor: William James King, Orange, CA (US)

( * ) Notice: Subject to any disclaimer, the term of this patent is extended or adjusted under 35 U.S.C. 154(b) by 48 days.

(21) Appl. No.: 16/283,350

(22) Filed: Feb. 22, 2019

(65) Prior Publication Data

US 2020/0268925 A1 Aug. 27, 2020

(51) Int. Cl.
*A61L 9/12* (2006.01)
*A61L 9/14* (2006.01)

(52) U.S. Cl.
CPC .................. *A61L 9/122* (2013.01); *A61L 9/14* (2013.01); *A61L 2209/111* (2013.01)

(58) Field of Classification Search
None
See application file for complete search history.

(56) References Cited

U.S. PATENT DOCUMENTS

2017/0253338 A1* 9/2017 Fantuzzi ............. B01F 3/04021
2018/0154036 A1* 6/2018 Davis ....................... A61L 9/122
2018/0280557 A1* 10/2018 Field ..................... B60H 3/0007

* cited by examiner

*Primary Examiner* — Jelitza M Perez
(74) *Attorney, Agent, or Firm* — Hahn Loeser & Parks LLP

(57) ABSTRACT

A portable air freshener device that inhibits the release of fragrance when the fan is not being operated, and that controls operation of the fan based at least in part on ambient temperature in some embodiments.

19 Claims, 6 Drawing Sheets

PORTABLE AIR FRESHENER DEVICE

FIELD OF THE INVENTION

The present disclosure generally relates to a portable air freshener device that inhibits the release of fragrance when the fan is not being operated, and that controls operation of the fan based at least in part on ambient temperature in some embodiments.

BACKGROUND AND SUMMARY

A problem with putting an air freshener in a confined space, such as the inside of a car, truck, boat, recreational vehicle, or other confined area, is that the fragrance can be released too quickly. This results in the aroma being stronger than desired, and in the fragrance source being dissipated too quickly. The present disclosure concerns better control of the release of the fragrance from the fragrance source, maximizing the usefulness of the air freshener device. A fan is controlled with intelligent programming which also results in power saving benefits, and a fragrance release shutter is disposed between the fan and the fragrance source. As used in the present application, fragrance release shutter is defined as a physical barrier, disposed between the fan and the fragrance source, that inhibits air flow to and from the fragrance source less when the fan is operating than when it is not operating.

BRIEF DESCRIPTION OF THE DRAWINGS

The following drawings illustrate the concepts of the present invention. Illustrations of an exemplary device are not necessarily drawn to scale.

DETAILED DESCRIPTION

Preferably, the components of the disclosed portable air freshener device are housed in a light-weight hard plastic, wood, or fiberglass case 50 that is compact and slim enough to be placed in narrow spaces, such as under a car seat, that might not be available for larger devices. For example, case 50 can be a rectangular cuboid with dimensions no greater than about 6 inches by about 2.5 inches by about 1.5 inches.

Figure 3:
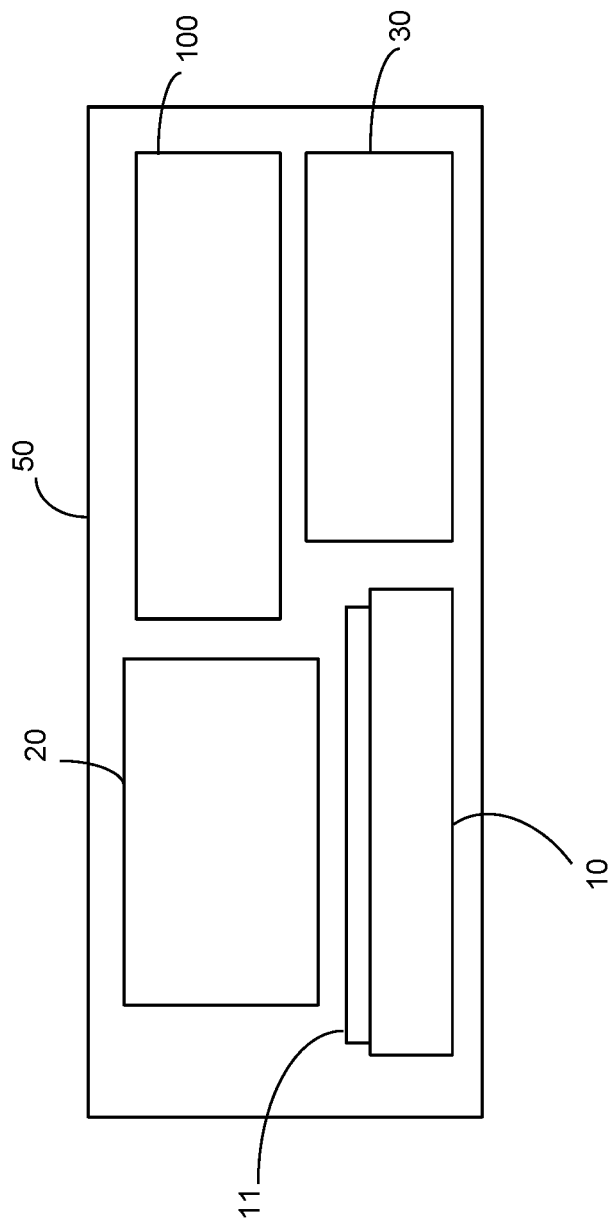
FIG. 3 is a cross-sectional view taken along 3-3 of FIG. 2.

FIG. 3 is a cross-sectional side view of one embodiment showing case 50 housing a solid fragrance material 10, a fan 20, a fragrance release shutter 11 disposed between the fan 20 and the solid fragrance material 10, a controller 100 that is programmed to control operation of the fan 20, and at least one battery 30 to power the fan.

Figure 2:
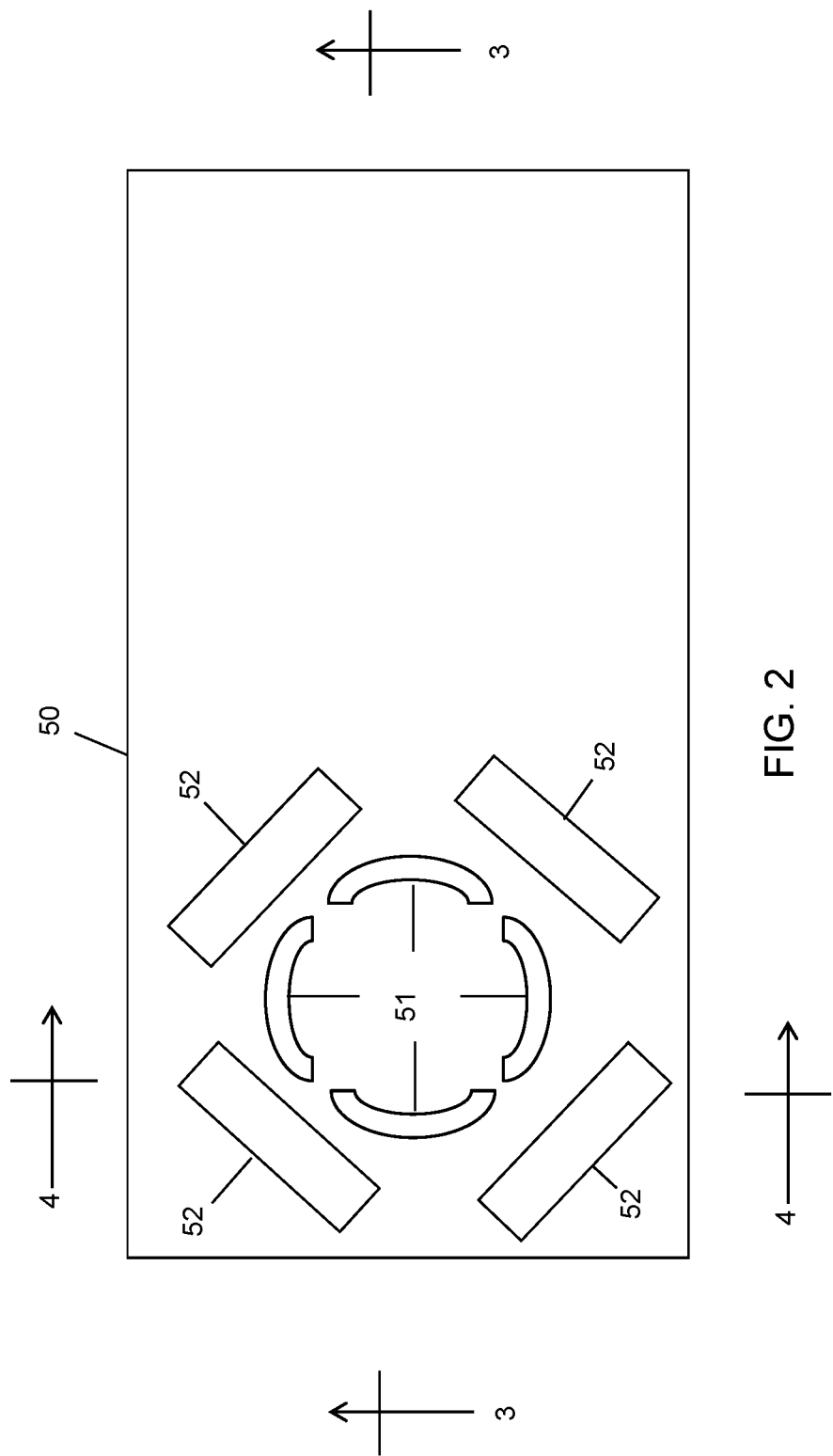
FIG. 2 is a top view of an embodiment of the disclosed portable air freshener device.
Figure 4:
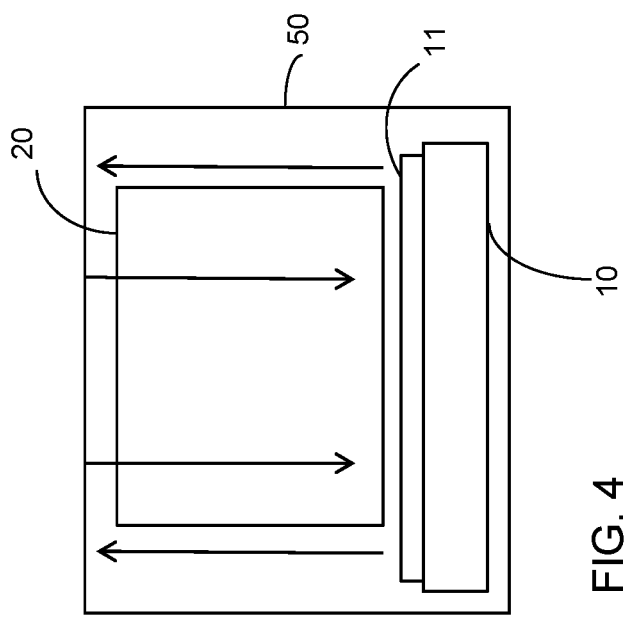
FIG. 4 is a cross-sectional view taken along 4-4 of FIG. 2.

FIG. 4 is a cross-sectional view cutting through case 50, fan 20, solid fragrance material 10, and fragrance release shutter 11. The arrows depict the direction of air flow when the fan 20 is operating, with air being drawn down through fan 20 towards the fragrance release shutter 11 and the solid fragrance material 10, and with scented air flowing up around the fan 20. As seen in FIG. 2 which is a top view of an exemplary embodiment of case 50, air is drawn down through intake openings 51 in the top of case 50, and scented air flows up through exhaust openings 52 in the top of case 50. This air flow design limits the release of fragrance when the fan 20 is not operating. This contributes to limiting the dissipation of the fragrance source without impeding the air freshening function of the device.

Figure 6:
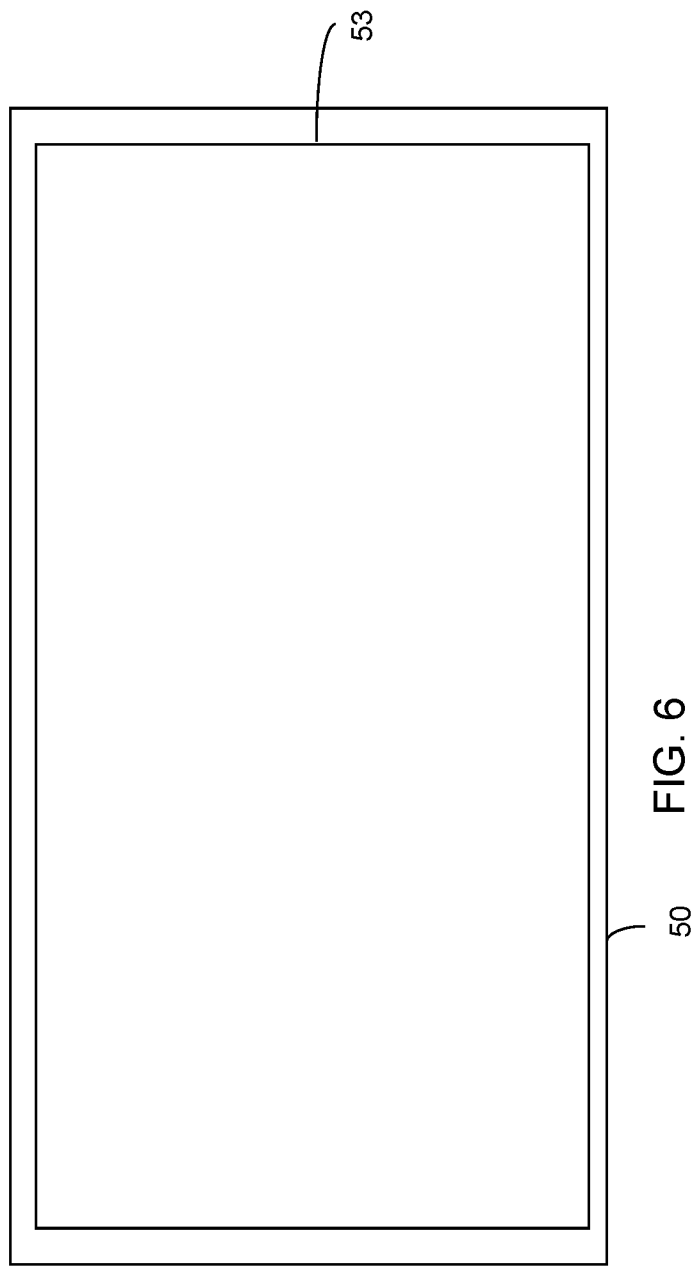
FIG. 6 is a bottom view of the embodiment of FIG. 2.

FIG. 6 is a bottom view of case 50, showing an example of a part 53, of a face of case 50, that is openable or removable to allow replacement of the at least one battery 30, or replacement of the solid fragrance material 10, or replacement of the solid fragrance material 10 and the fragrance release shutter 11; and that is closable and restorable for resumption of normal operation of the air freshener device. In different respective embodiments, the part 53 can be hinged, secured with fasteners, clamped, snap-fit, friction-fit, and so forth. In some embodiments, there can be different parts 53, such as with one allowing replacement of the solid fragrance material 10 and another allowing replacement of the at least one battery 30.

The solid fragrance material 10 can take different forms such as, for example, scented tallow, a scented block, or scented beads. It can take different shapes such as, for example, cylindrical or that of a rectangular cuboid. Any scent can be used according to the preference of the user. As an example, various solid fragrance materials 10 are commercially available from Air Scent International in Pittsburgh, Pa.

Figure 7:
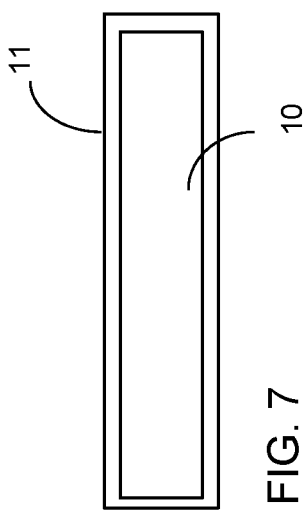
FIG. 7 is a side view of an embodiment of a packaged fragrance source material.
Figure 8:
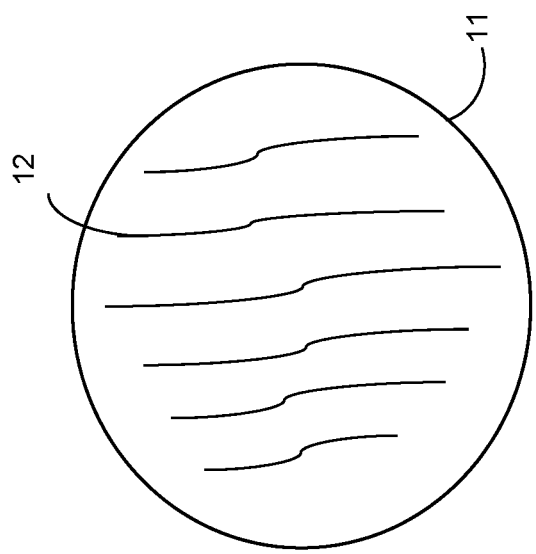
FIG. 8 is a top view of the embodiment of FIG. 7, with slits in the packaging material converting the packaging to a fragrance release shutter.

The fragrance release shutter 11 is a physical barrier, disposed between the fan 20 and the solid fragrance material 10, that inhibits air flow to and from the solid fragrance material 10 less when the fan 20 is operating than when it is not operating. There are many air filter materials that can be used such as foam, cotton, or paper materials. One fragrance release shutter 11 that has worked well is to cut slits 12 in one face of cellophane packaging or material surrounding a solid fragrance material 10. This is illustrated in FIGS. 7 and 8, FIG. 7 being a side view of an embodiment of a packaged solid fragrance material 10 and FIG. 8 being a top view showing slits in the packaging to convert the packaging to a fragrance release shutter 11. Forced air from the fan 20 tends to keep the slits 12 open and the air flowing to and from the solid fragrance material 10, and the slits 12 tend to close inhibiting air flow to and from the solid fragrance material 10 when the fan 20 is not operating. However, the most preferred fragrance release shutter 11 is burlap spread over the solid fragrance material 10. The burlap works well to inhibit air flow to and from the solid fragrance material 10 less when the fan 20 is operating than when it is not operating. This contributes to limiting the dissipation of the fragrance source without impeding the air freshening function of the device.

In some embodiments, the fan 20 may be powered from sources other than a battery, such as through power plug. In some embodiments in which there is at least one battery 30, the at least one battery 30 can be rechargeable. In some embodiments in which the at least one battery 30 is rechargeable, the portable air freshener device includes recharging circuitry 31 for recharging the at least one battery and a recharging port 32 through which power can be supplied to the recharging circuitry 31. In some embodiments, the recharging port 32 can be a Universal Serial Bus (USB) input port. This allows the device to receive power, for example, from a computer, from an automobile dashboard DC voltage receptacle with appropriate electrical connections, or from wall power with appropriate rectification.

Controller 100 controls operation of the fan 20, and can be programmed to limit the dissipation of the fragrance source without impeding the air freshening function of the device. The controller 100 comprises control logic circuitry 40. In conjunction with a clock 44, operation of the fan 20 can be based at least in part on at least one parameter selected from a group consisting of ambient temperature, time of day, duration of time that the fan 20 has been operating continuously, and duration of time that the fan 20 has been operating during a predetermined period of time.

In some embodiments, the portable air freshener device includes temperature sensor 43, to provide a signal representative of ambient temperature used by the control logic circuitry 40 in controlling operation of the fan 20. Fragrance typically is released from a fragrance source at a greater rate when the temperature is higher, so controller 100 can be programmed to limit operation of the fan 20 or possibly to reduce fan speed at certain temperatures. Temperature sensor 43 can be included within controller 100 or can be a separate component.

Figure 1:
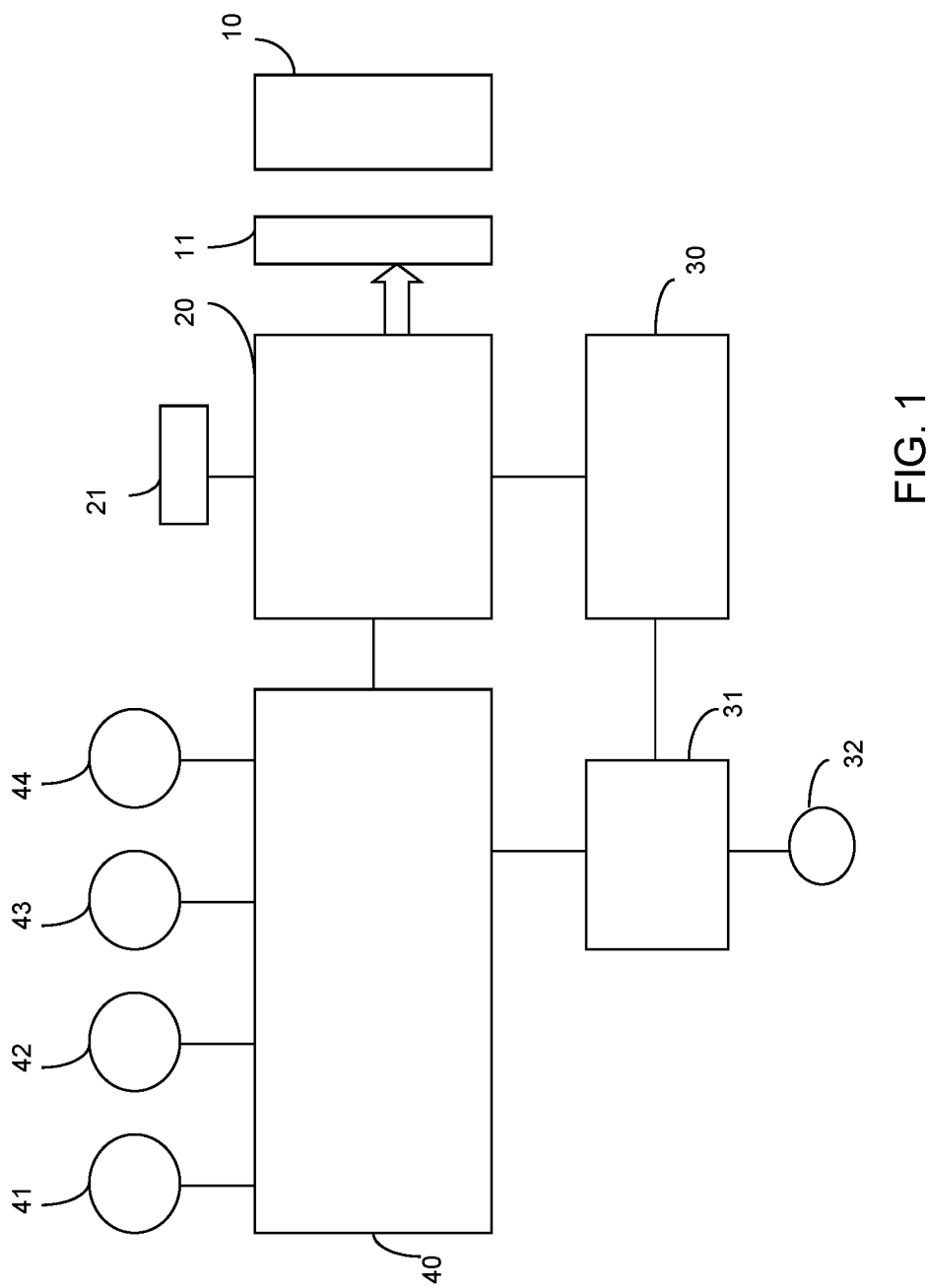
FIG. 1 is a functional block diagram that represents the functions of an embodiment of the disclosed portable air freshener device.
Figure 5:
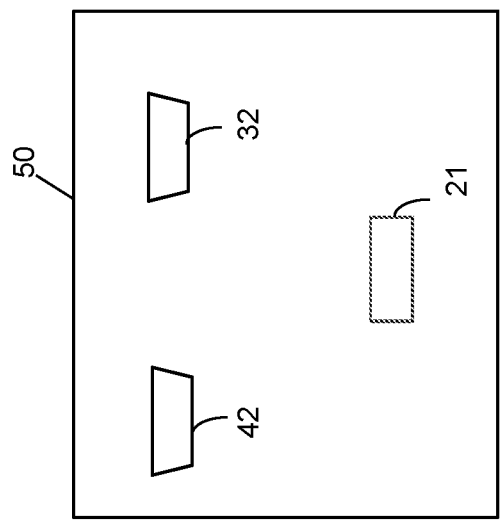
FIG. 5 is a side view, illustrating one end of the embodiment of FIG. 2.

In some embodiments, control logic circuitry 40 can be programmed with external instructions or can receive information such as time, temperature, or an on-off command from an external source. Such instructions or information can be provided through a communications port 42 or through a wireless transceiver 41. For example, communications port 42 can be a USB input port and, in some embodiments, can be the same port as recharging port 32. For example, transceiver 41 can use Bluetooth® wireless technology. Wireless transceiver 41 can be included within controller 100 or can be a separate component. In some embodiments, there also can be a manual on-off switch 21 to prevent operation of the fan 20. Recharging circuitry 31 can be included within controller 100 or in a separate component. FIG. 5 illustrates an end of case 50, showing a recharging port 32, a communications port 42, and a manual switch 21. FIG. 1 is a functional block diagraph representing the different functions discussed above. As an example, a controller 100 that includes a transceiver 41, a temperature sensor 43, and recharging circuitry 31 and that can be programmed as discussed above is commercially available as part number 10930 from Phenix Controls Inc. in Santa Ana, Calif.

It will be understood that the disclosed portable air freshener device can be modified without departing from the teachings of the invention. Accordingly, the scope of the invention is only to be limited as necessitated by the accompanying claims.

What is claimed is:

1. A portable air freshener device, comprising:
   a solid fragrance material;
   a fan;
   a fragrance release shutter disposed between the fan and the solid fragrance material, wherein forced air flow due to operation of the fan causes the fragrance release shutter to inhibit air flow to and from the solid fragrance material less when the fan is operating than when it is not operating; and,
   a controller that is programmed to control operation of the fan.

2. The portable air freshener device of claim 1, further comprising:
   a temperature sensor;
   wherein the operation of the fan is controlled, at least in part, based on a signal from the temperature sensor.

3. The portable air freshener device of claim 1, wherein the fragrance release shutter comprises burlap.

4. The portable air freshener device of claim 1, wherein the fragrance release shutter comprises cellophane, with slits in the cellophane that open or open wider when the fan is being operated.

5. The portable air freshener device of claim 1, further comprising at least one battery to power the fan.

6. The portable air freshener device of claim 5, wherein the at least one battery is rechargeable.

7. The portable air freshener device of claim 6, further comprises:
   recharging circuitry for recharging the at least one battery; and
   a recharging port through Which power can be supplied to the recharging circuitry.

8. The portable air freshener device of claim 7, wherein the recharging port comprises a universal serial bus input port.

9. The portable air freshener device of claim 1, further comprising a communications port for receiving information used to control the operation of the fan.

10. The portable air freshener device of claim 1, further comprising a wireless transceiver for receiving information used to control the operation of the fan.

11. The portable air freshener device of claim 1, wherein the controller is programmed to control the operation of the fan based at least in part on at least one parameter selected from a group consisting of ambient temperature, time of day, duration of time that the fan has been operating continuously, and duration of time that the fan has been operating during a predetermined period of time.

12. The portable air freshener device of claim 1, wherein the controller is programmed to control the operation of the fan based at least in part on ambient temperature.

13. The portable air freshener device of claim 1, further comprising a manual switch to prevent the operation of the fan.

14. The portable air freshener device of claim 1, wherein the solid fragrance material is selected from a group consisting of scented tallow, a scented block, and scented beads.

15. The portable air freshener device of claim 1, further comprising:
   a case that houses the solid fragrance material, the fan, the fragrance release shutter, and the controller;
   wherein at least part of one face of the case is openable or removable to allow replacement of the solid fragrance material, and is closable or restorable for resumption of normal operation of the air freshener device.

16. The portable air freshener device of claim 1, further comprising:
   at least one battery to power the fan;
   a case that houses the solid fragrance material, the fan, the fragrance release shutter, the at least one battery, and the controller;
   wherein at least part of one face of the case is openable or removable to allow replacement of the at least one battery, and is closable or restorable for resumption of normal operation of the air freshener device.

17. The portable air freshener device of claim 1, further comprising:
   at least one battery to power the fan;

a case that houses the solid fragrance material, the fan, the fragrance release shutter, the at least one battery, and the controller, the case being substantially a rectangular cuboid with dimensions no greater than about 6 inches by about 2.5 inches by about 1.5 inches.

18. A method of controlling release of fragrance from a portable air freshener device comprising a solid fragrance material, a fan, and a controller for controlling operation of the fan, the method comprising:
   disposing a fragrance release shutter between the fan and the solid fragrance material to inhibit the release of the fragrance from the solid fragrance material when the fan is not being operated; and
   controlling operation of the fan to force or not to force air flow, wherein the forced air flow causes the fragrance release shutter to inhibit air flow to and from the solid fragrance material less than when there is no forced air flow.

19. The method of claim 18, further comprising:
   programming the controller to control the operation of the fan based at least in part on ambient temperature.

\* \* \* \* \*

UNITED STATES PATENT AND TRADEMARK OFFICE
CERTIFICATE OF CORRECTION

PATENT NO. : 10,987,446 B2  
APPLICATION NO. : 16/283350  
DATED : April 27, 2021  
INVENTOR(S) : King Page 1 of 1

It is certified that error appears in the above-identified patent and that said Letters Patent is hereby corrected as shown below:

In the Claims

In Column 3, Line 65 (ninth line of Claim 1), delete "and," and insert therefor --and--.

In Column 4, Line 20 (fifth line of Claim 7), delete "Which" and insert therefor --which--.

Signed and Sealed this
First Day of June, 2021

Drew Hirshfeld
*Performing the Functions and Duties of the*
*Under Secretary of Commerce for Intellectual Property and*
*Director of the United States Patent and Trademark Office*